(12) United States Patent
Cao et al.

(10) Patent No.: US 11,360,171 B2
(45) Date of Patent: Jun. 14, 2022

(54) METHOD FOR OBTAINING MAGNETIC RESONANCE IMAGING DATA AND MAGNETIC RESONANCE IMAGING SYSTEM

(71) Applicant: GE Precision Healthcare LLC, Wauwatosa, WI (US)

(72) Inventors: Nan Cao, Beijing (CN); Yongchuan Lai, Beijing (CN); Pengfei Lu, Beijing (CN)

(73) Assignee: GE Precision Healthcare LLC, Wauwatosa, WI (US)

( * ) Notice: Subject to any disclaimer, the term of this patent is extended or adjusted under 35 U.S.C. 154(b) by 0 days.

(21) Appl. No.: 16/849,582

(22) Filed: Apr. 15, 2020

(65) Prior Publication Data

US 2020/0341088 A1    Oct. 29, 2020

(30) Foreign Application Priority Data

Apr. 24, 2019  (CN) .......................... 201910336290.X

(51) Int. Cl.
| | | |
|---|---|---|
| *G01V 3/00* | (2006.01) | |
| *G01R 33/48* | (2006.01) | |
| *G01R 33/56* | (2006.01) | |
| *A61B 5/055* | (2006.01) | |
| *G01R 33/561* | (2006.01) | |
| *G01R 33/54* | (2006.01) | |

(52) U.S. Cl.
CPC .......... *G01R 33/4828* (2013.01); *A61B 5/055* (2013.01); *G01R 33/543* (2013.01); *G01R 33/5607* (2013.01); *G01R 33/5608* (2013.01); *G01R 33/5615* (2013.01)

(58) Field of Classification Search
CPC .............. G01R 33/543; G01R 33/5659; G01R 33/3415; G01R 33/36; A61B 5/055
USPC ........................................................ 324/309
See application file for complete search history.

(56) References Cited

U.S. PATENT DOCUMENTS

| | | | |
|---|---|---|---|
| 6,448,773 B1 * | 9/2002 | Zhang .............. | G01R 33/56518 324/307 |
| 6,466,014 B1 | 10/2002 | Ma | |
| 7,084,626 B2 | 8/2006 | Ma | |
| 8,587,305 B2 | 11/2013 | Madhuranthakam | |

(Continued)

FOREIGN PATENT DOCUMENTS

| | | | | |
|---|---|---|---|---|
| DE | 112015006200 T5 * | 11/2017 | ......... | G01R 33/5602 |
| JP | 406007314 A * | 1/1994 | ............. | G01R 33/48 |

(Continued)

OTHER PUBLICATIONS

Usai JP 406007314A (Year: 1994).*

*Primary Examiner* — Walter L Lindsay, Jr.
*Assistant Examiner* — Frederick Wenderoth

(57) ABSTRACT

Embodiments of the present invention provide a magnetic resonance imaging system and a method for obtaining magnetic resonance imaging data. The method comprises: applying a fat suppression pulse before the start of any repetition time of an imaging sequence; performing a plurality of echoes in the repetition time, wherein first image data when water and fat are in phase and second image data when water and fat are out of phase are obtained during each echo of the plurality of echoes; and obtaining fat-suppressed image data according to the first image data and the second image data.

18 Claims, 6 Drawing Sheets

(56) References Cited

U.S. PATENT DOCUMENTS

| | | | |
|---|---|---|---|
| 8,879,852 B2* | 11/2014 | Chang | A61B 5/055 |
| | | | 382/206 |
| 9,575,154 B2 | 2/2017 | Simonetti | |
| 2004/0032977 A1 | 2/2004 | Blezek | |
| 2008/0204020 A1* | 8/2008 | Chamberlain | G01R 33/56527 |
| | | | 324/312 |
| 2008/0218169 A1 | 9/2008 | Bookwalter | |
| 2014/0043022 A1 | 2/2014 | Geerts-Ossevoort | |
| 2016/0154081 A1* | 6/2016 | Chung | G01R 33/543 |
| | | | 324/309 |
| 2017/0363699 A1* | 12/2017 | Ookawa | G01R 33/4831 |

FOREIGN PATENT DOCUMENTS

| | | |
|---|---|---|
| WO | 2003098267 A1 | 11/2003 |
| WO | 2003100465 A1 | 12/2003 |

\* cited by examiner

FIG. 2 (DRAWING FOR ABSTRACT)

METHOD FOR OBTAINING MAGNETIC RESONANCE IMAGING DATA AND MAGNETIC RESONANCE IMAGING SYSTEM

CROSS-REFERENCE TO RELATED APPLICATIONS

This application claims the benefit of French Patent Application No. 201910336290.X filed on Apr. 24, 2019, the disclosure of which is herein incorporated by reference in its entirety.

TECHNICAL FIELD

Embodiments disclosed in the present invention relate to medical imaging technologies, and more specifically to a method for obtaining magnetic resonance imaging data and a magnetic resonance imaging system.

BACKGROUND

As a medical imaging modality, Magnetic resonance imaging (MRI), can obtain images of the human body without using X-rays or other ionizing radiation. MRI uses a magnet having a strong magnetic field to generate a static magnetic field B0. When a part of the human body to be imaged is positioned in the static magnetic field B0, nuclear spin associated with hydrogen nuclei in human tissue is polarized, so that the tissue of the to-be-imaged part generates a longitudinal magnetization vector at a macroscopic level. After a radio-frequency field B1 intersecting the direction of the static magnetic field B0 is applied, the direction of rotation of protons changes so that the tissue of the to-be-imaged part generates a transverse magnetization vector at a macroscopic level. After the radio-frequency field B1 is removed, the transverse magnetization vector decays in a spiral manner until it is restored to zero. A free induction decay signal is generated during decay. The free induction decay signal can be acquired as a magnetic resonance signal, and a tissue image of the to-be-imaged part can be reconstructed based on the acquired signal.

Due to different precession frequencies of protons in water and fat in human tissue, chemical shift artifacts are produced during magnetic resonance imaging. In order to remove the chemical shift artifacts or other artifacts caused by fat tissue, or to meet some specific clinical diagnostic requirements, many fat suppression methods are proposed in the prior art, but it is still difficult to obtain an ideal water tissue image, especially when the static magnetic field B0 or the radio-frequency field B1 is inhomogeneous.

The prior art proposes an improved fat suppression method, namely, obtaining image data when water tissue and fat tissue are in phase during one repetition time of an imaging sequence, and obtaining image data when water tissue and fat tissue are out of phase during another repetition time of the imaging sequence, and then obtaining image data of pure water through an image processing algorithm. Although this method can obtain a water tissue image with better image quality, the scan time is relatively longer and the process lacks simplicity because two repetition times are required to obtain the required image.

Accordingly, a novel method for obtaining magnetic resonance imaging data needs to be provided—a method that can obtain an image within a short scan time and can effectively remove various artifacts in the image produced by chemical shift.

SUMMARY

One embodiment of the present invention provides a method for obtaining magnetic resonance imaging data, the method comprising: applying a fat suppression pulse before the start of any repetition time of an imaging sequence; performing a plurality of echoes in the repetition time, wherein first image data when water and fat are in phase and second image data when water and fat are out of phase are obtained during each echo of the plurality of echoes; and obtaining fat-suppressed image data according to the first image data and the second image data.

One embodiment of the present invention provides a magnetic resonance imaging system, comprising: a scanner, the scanner used for obtaining data of an imaging object; a controller unit, the controller unit coupled to the scanner and used for controlling the scanner to perform an imaging sequence, wherein a fat suppression pulse is applied before the start of any repetition time of the imaging sequence; and a plurality of echoes are performed in the repetition time, wherein first image data when water and fat are in phase and second image data when water and fat are out of phase are obtained during each echo of the plurality of echoes; and a data processing unit, used for obtaining fat-suppressed image data according to the first image data and the second image data.

It should be understood that the brief description above is provided to introduce in simplified form some concepts that will be further described in the detailed description of the Embodiments. The brief description above is not meant to identify key or essential features of the claimed subject matter. The protection scope is defined uniquely by the claims that follow the detailed description. Furthermore, the claimed subject matter is not limited to implementations that solve any disadvantages noted above or in any section of the present disclosure.

BRIEF DESCRIPTION OF THE DRAWINGS

The present invention will be better understood by reading the following description of non-limiting embodiments with reference to the accompanying drawings, where.

DETAILED DESCRIPTION

Various embodiments described below include a method for obtaining data from an imaging object (for example, a human body) by an imaging system (such as the magnetic resonance imaging (MRI) system in FIG. 1). By means of the method, the image obtained by image reconstruction based on the data has a better fat suppression effect, for example, having reduced artifacts caused by fat signals such as chemical shift artifacts or chemical shift edge artifacts.

Figure 2:
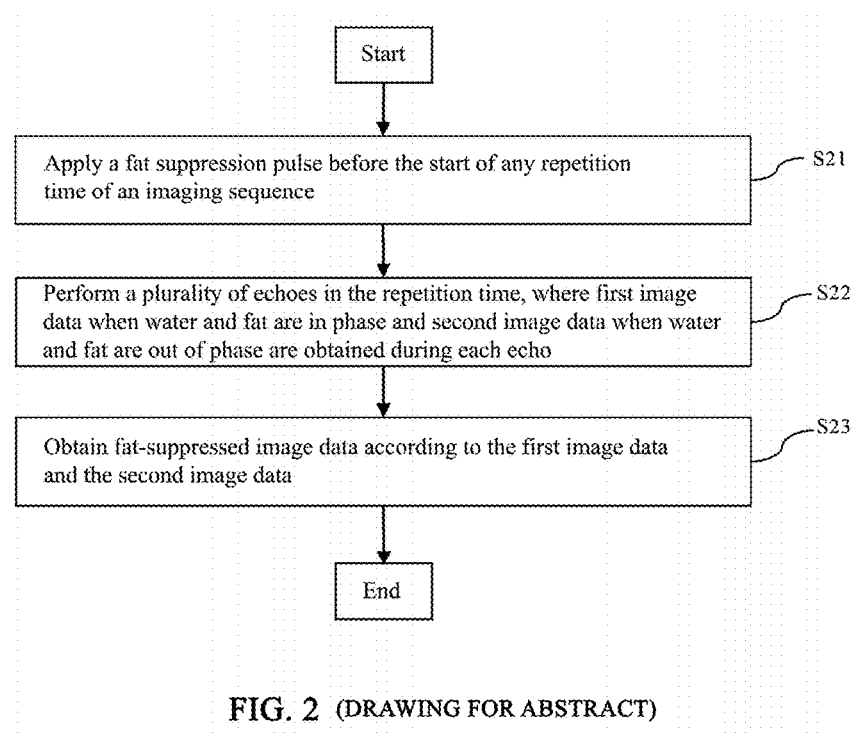
FIG. 2 is a flowchart of a method for obtaining magnetic resonance image data according to one embodiment of the present invention.

FIG. 2 is a flowchart of a method for obtaining medical image data according to one embodiment. As shown in FIG. 2, the method includes steps S21 and S22 and step S23.

Step S21: Apply a fat suppression pulse before the start of any repetition time of an imaging sequence.

Those skilled in the art can understand that the imaging sequence refers to a combination of pulses having specific amplitudes, widths, directions, and time sequences and applied when MRI is performed, where the pulses may include, for example, a radio-frequency pulse and a gradient pulse. The radio-frequency pulse may include, for example, a radio-frequency excitation pulse for exciting protons in the human body to resonate, and the gradient pulse may include, for example, a slice selection gradient pulse, a phase encoding gradient pulse, and a frequency encoding gradient pulse. In one embodiment, the repetition time refers to a time interval between two adjacent radio-frequency excitation pulses of the imaging sequence.

Step S22: Perform a plurality of echoes in the repetition time, where first image data when water and fat are in phase and second image data when water and fat are out of phase are obtained during each echo of the plurality of echoes.

Step S23: Obtain fat-suppressed image data according to the first image data and the second image data.

In the embodiment of the present invention, a fat suppression pulse is applied prior to a repetition time, so that a fat tissue signal is suppressed or has decreased strength during the repetition time, and thus no magnetic resonance signal of fat tissue is generated or a weak magnetic resonance signal of fat tissue is generated; further, both first image data when water and fat are in phase and second image data when water and fat are out of phase are obtained in the same repetition time, so that two kinds of data can be acquired in a short time, and image data with one kind of tissue suppressed can be obtained according to the two kinds of data, thereby achieving a desirable artifact removal effect without increasing the scan time.

In one embodiment, during each echo, a first gradient read pulse is applied when water and fat are in phase to obtain the first image data, and a second gradient read pulse is applied when water and fat are out of phase to obtain the second image data. The aforementioned gradient read pulse is a frequency encoding gradient pulse, where the pulse is responded to so that a magnetic resonance signal with position information can be acquired.

Figure 3:
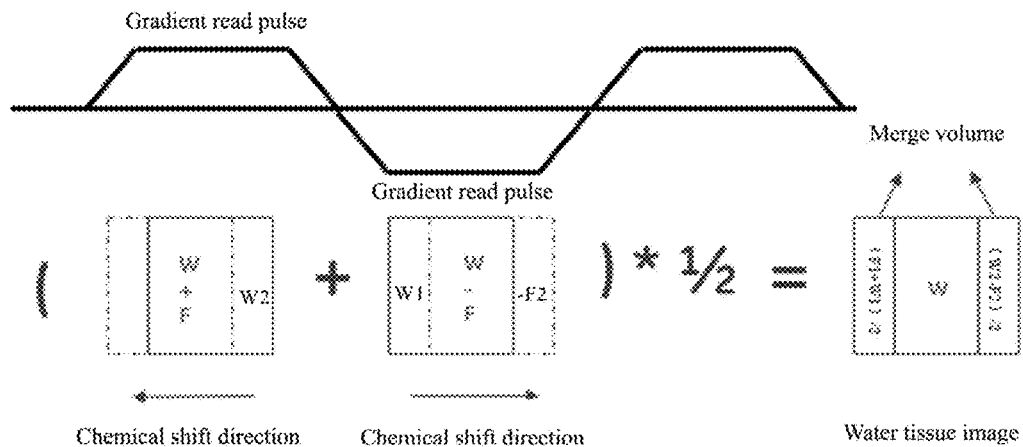
FIG. 3 is a schematic diagram illustrating analysis of first image data and a second image having opposite chemical shift directions.

Further, the first image data and the second image data obtained during each echo have opposite chemical shift directions. In this way, chemical shift edge artifacts can be further removed. Due to the chemical shift of water and fat tissue, the fat tissue in the image is shifted to one side. When two kinds of image data are obtained in the same repetition time, the edge of an imaged part in the image consequently has a bright signal on one side and a dark signal on the other side. Using FIG. 3 as an example, the chemical shift direction is reversed so that the edge on each side has a water signal and a fat signal (for example, the left side of the data is $(W+F)/2$ rather than $(F+F)/2$, and the right side of the data is $(W-F)/2$ rather than $(W-W)/2$), thereby reducing brightness difference of the edges and achieving a more homogeneous image.

For example, the fat-suppressed image data may be obtained through the following equations (1) to (3).

$$I1 = F1 + W + F + W2 \quad (1)$$

$$I2 = W1 + W - F - F2 \quad (2)$$

$$I3 = (I1 + I2)/2 = (F1 + W1)/2 + 2*W/2 + (W2 - F2)/2 \quad (3), \text{where}$$

I1 and I2 are respectively the first image data and the second image data, and I3 is water tissue image data with fat tissue suppressed; W represents a water tissue signal in the middle region of the image; F represents a fat tissue signal in the middle region of the image; W1 and W2 respectively represent water tissue signals at edges on two sides (for example, the left side and the right side) of the image; F1 and F2 respectively represent fat tissue signals at edges on two sides (for example, the left side and the right side) of the image.

Further, since a fat suppression pulse is applied prior to a repetition time, the fat signals F1 and F2 would be extremely low in when fat tissue signals have extremely low strength. At this time, $I3 \approx W1/2 + W + W2/2$. Therefore, an image with higher quality can be obtained, where a desirable fat suppression effect is achieved. Chemical shift artifacts, chemical shift edge artifacts, and other image problems caused by fat signals would be effectively removed.

In one embodiment, the first gradient read pulse and the second gradient read pulse may have opposite directions so that the first image data and the second image data have opposite chemical shift directions.

Further, the first gradient read pulse and the second gradient read pulse are continuously applied. With this design, both first image data and second image data can be obtained in one echo period, so as to reduce the scan time.

Further, a first gradient read pulse is applied once and a second gradient read pulse is applied twice respectively before and after the first gradient read pulse during each echo. In this symmetrical way, a balanced read gradient area can be ensured, and both first image and second image data can be obtained in one echo period, so as to reduce the scan time.

When a second gradient read pulse is applied twice during each echo to obtain two pieces of second image data, the fat-suppressed image data is obtained according to average image data of the two pieces of second image data obtained when the second gradient read pulse is applied twice and the first image data. Specifically, the second image data I2 mentioned in the aforementioned equations (1) and (3) is obtained after data averaging is performed on two sets of image data obtained under the same gradient read pulse.

Figure 4:
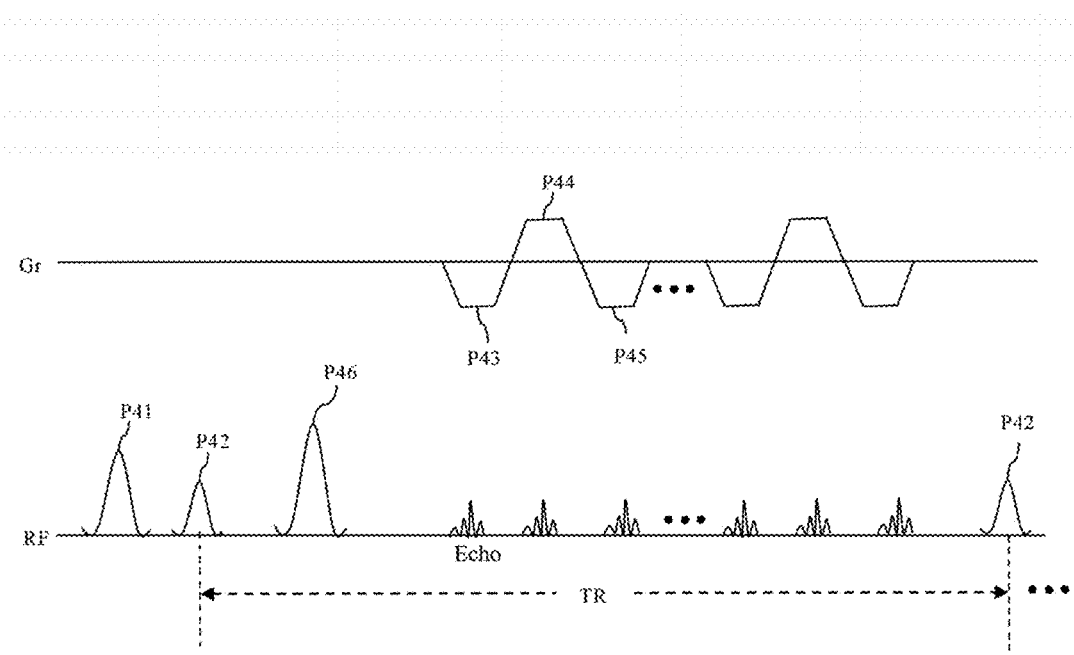
FIG. 4 illustrates an example of an imaging sequence used for the method shown in FIG. 2 according to an embodiment of the present invention.

FIG. 4 illustrates an example of an imaging sequence used for the aforementioned method according to an embodiment of the present invention, where at least some sequence waveforms of at least one repetition time of the imaging sequence are shown.

As shown in FIG. 4, the imaging sequence includes a fat suppression pulse P41 applied prior to any repetition time TR, and in the repetition time TR, gradient read pulses P43, P44, and P45 are sequentially applied after the end of an applied radio-frequency excitation pulse P42, where the gradient read pulses P43, P44, and P45 have preferably the same amplitude and width, and the gradient read pulse P44 has a direction opposite to that of the gradient read pulses P43 and P45. The gradient read pulse P44 may be used as the aforementioned first gradient pulse, and applied when water and fat are in phase. The gradient read pulses P43 and P45 may be respectively used as the aforementioned second gradient pulses and applied when water and fat are out of phase.

The imaging sequence in this example may further include other pulses. These other pulses may be, for example, located between any two adjacent pulses in FIG. 3, for example, a radio-frequency refocusing pulse P46 applied after the end of the radio-frequency excitation pulse P41. The example of the present invention is used only for illustrating the sequential relationship between the pulses shown in FIG. 3, rather than limiting the sequential relationship between these pulses and other pulses not shown.

In the above example, the radio-frequency excitation pulse may be, for example, a 90-degree radio-frequency pulse, and the fat suppression pulse may be one or more of a frequency selection suppression pulse, a spatial presaturation pulse, a reverse fat suppression pulse, or a heat insulation pulse.

FIG. 4 shows only one form of the imaging sequence that can be applied to the aforementioned method. It is not intended for FIG. 4 to limit the protection scope of the present invention.

Figure 1:
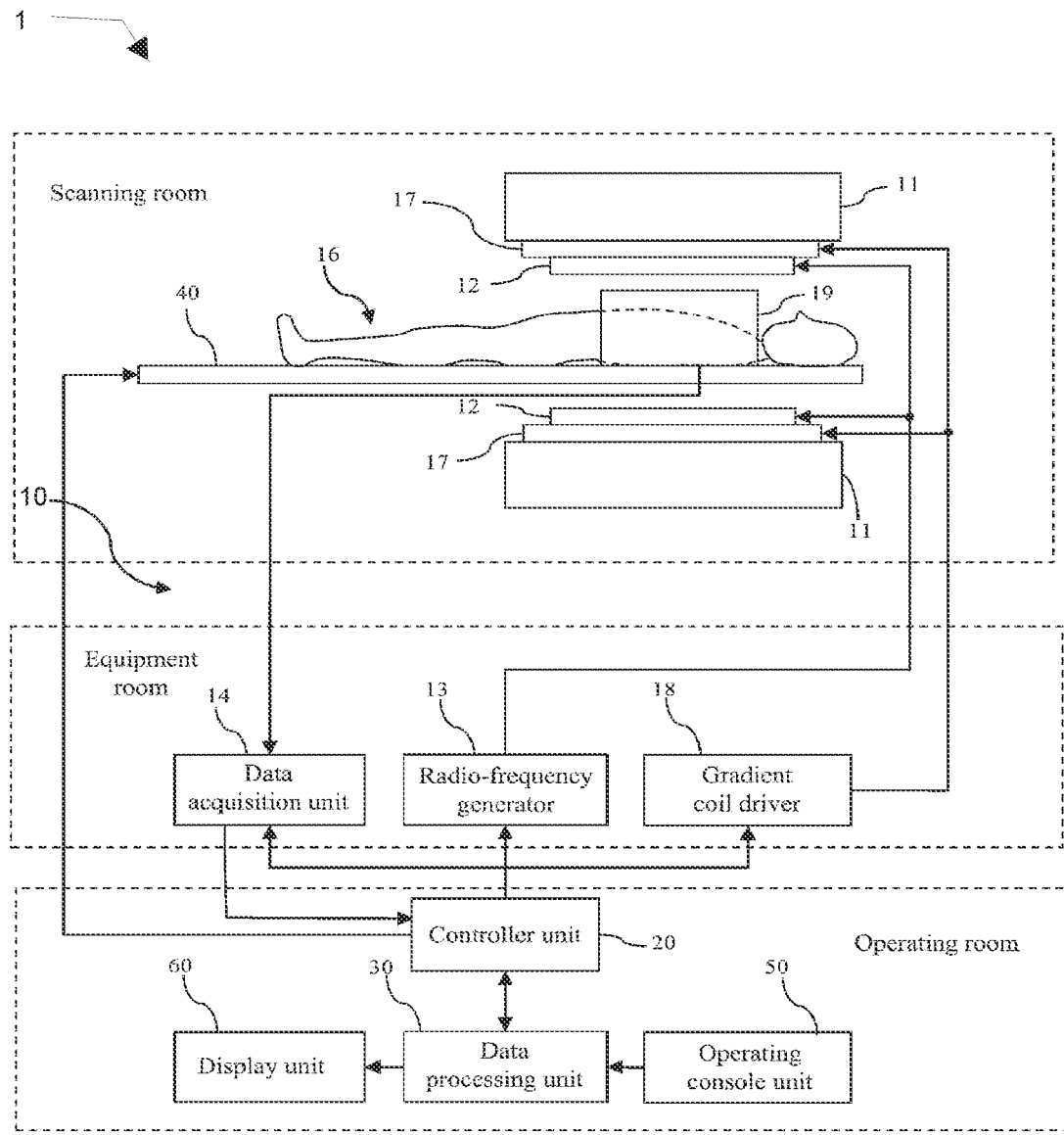
FIG. 1 is a block diagram of a magnetic resonance imaging system according to one embodiment.

The aforementioned method for obtaining magnetic resonance image data may be implemented by, for example, the magnetic resonance (MRI) system 1 shown in FIG. 1. In other embodiments, the MRI system 1 is described only as an example. In other embodiments, the MRI system 1 may have a plurality of transformations, as long as image data can be acquired from an imaging object.

As shown in FIG. 1, the MRI system 1 includes at least a scanner 10, a controller unit 20, and a data processing unit 30. The scanner 10 may be used for obtaining data of an imaging object. The controller unit 20 is coupled to the scanner 10 and used for controlling the operation of the scanner 10, for example, controlling the scanner 10 to perform the aforementioned steps S21 to S22, where a fat suppression pulse is applied before the start of any repetition time of an imaging sequence; and a plurality of echoes are performed in the repetition time, where first image data when water and fat are in phase and second image data when water and fat are out of phase are obtained during each echo of the plurality of echoes. The data processing unit 30 may be used for obtaining fat-suppressed image data according to the first image data and the second image data.

In an example, the scanner 10 may include components disposed in a scanning room and components in an equipment room. For example, the scanner 10 includes a main magnet 11, an RF transmit coil 12, a radio-frequency generator 13, a gradient coil system 17, a gradient coil driver 18, and an RF receive coil 19.

The main magnet 11 usually includes, for example, an annular superconducting magnet, where the annular superconducting magnet is mounted in an annular vacuum container. The annular superconducting magnet defines a cylindrical space surrounding an object 16. Moreover, a constant static magnetic field, such as a static magnetic field B0, is generated along a Z direction of the cylindrical space. The MRI system 1 uses the formed static magnetic field B0 to emit a magnetostatic pulse signal to an object 16 placed in the imaging space, so that the precession of protons in the body of the object 16 is ordered to generate a longitudinal magnetization vector.

The radio-frequency generator 13 is used for generating a radio-frequency pulse. The radio-frequency pulse may include a radio-frequency excitation pulse. The radio-frequency excitation pulse is amplified (by, for example, a radio-frequency power amplifier (not shown)) and then applied to the RF transmit coil 12, so that the RF transmit coil 12 emits to the object 16 an RF magnetic field B1 orthogonal to the static magnetic field B0 to excite nuclei in the body of the object 16, and the longitudinal magnetization vector is converted into a transverse magnetization vector.

After the end of the radio-frequency excitation pulse, a free induction decay signal (i.e., a magnetic resonance signal that can be acquired) is generated in the process that the transverse magnetization vector of the object 16 is gradually restored to zero.

The radio-frequency pulse may further include pulses having other functions, such as a radio-frequency pulse for suppressing a specific tissue signal (more specifically, a fat suppression pulse). When the fat suppression pulse is applied before the radio-frequency excitation pulse is applied, the fat tissue is not excited after the radio-frequency excitation pulse is applied, so that an acquired magnetic resonance signal does not include a fat tissue signal or includes only a small fat tissue signal.

The radio-frequency generator 13 may be used for generating the radio-frequency excitation pulse or fat suppression pulse in response to an imaging sequence control signal sent by the controller unit 20.

In one embodiment, the RF transmit coil 12 may be a body coil that may be connected to a transmit/receive (T/R) switch (not shown). The transmit/receive (T/R) switch is controlled so that the body coil can be switched between a transmit mode and a receive mode. In the receive mode, the body coil may be used for receiving the magnetic resonance signal from the object 16.

The scanner 10 may further include a gradient coil system 17 and a gradient driver 18. The gradient coil system 17 forms a gradient magnetic field in the imaging space so as to provide three-dimensional position information to the magnetic resonance signal. The magnetic resonance signal may be received by the RF receive coil 19 or the body coil in the receive mode. The data processing unit 30 may process the received magnetic resonance signal to obtain the required image or image data.

Specifically, the gradient coil system 17 may include three gradient coils. Each of the three gradient coils generates a gradient magnetic field that is inclined to one of three spatial axes (for example, X-axis, Y-axis, and Z-axis) perpendicular to each other, and generates a gradient field according to imaging conditions in each of a slice selection direction, a phase encoding direction, and a frequency encoding direction. More specifically, the gradient coil system 17 applies a gradient field in the slice selection direction of the object 16 so as to select a slice; and the RF transmit coil 12 emits the RF excitation pulse to the slice selected by the object 16 and excites the slice. The gradient coil system 17 also applies a gradient field in the phase encoding direction of the object 16 so as to perform phase encoding on a magnetic resonance signal of the excited slice. The gradient coil system 17 then applies a gradient field in the frequency encoding direction of the object 16 so as to perform frequency encoding on the magnetic resonance signal of the excited slice.

The gradient coil driver 18 is used for providing a suitable power signal to each of the aforementioned three gradient coils in response to the sequence control signal sent by the controller unit 30.

The scanner 10 may further include a data acquisition unit 14 that is used for acquiring a magnetic resonance signal received by the RF surface coil 19 or the body coil. The data acquisition unit 14 may include, for example, a radio-frequency preamplifier (not shown), a phase detector (not shown), and an analog/digital converter (not shown), where the radio-frequency preamplifier is used for amplifying the magnetic resonance signal received by the RF surface coil 19 or the body coil, the phase detector is used for performing phase detection on the amplified magnetic resonance signal, and the analog/digital converter is used for converting the phase-detected magnetic resonance signal from an analog signal to a digital signal.

The digitized magnetic resonance signal may be processed, for example calculated or reconstructed, by the data processing unit 30. The data processing unit 30 may include a computer and a storage medium, where a program of predetermined data processing to be executed by the computer is recorded on the storage medium. The data processing unit 30 may be connected to the controller unit 20 and perform data processing based on the control signal received from the controller unit 20. The data processing unit 30 may also be connected to the data acquisition unit 14 to receive the magnetic resonance signal output by the data acquisition unit 14 so as to perform the data processing described above.

The controller unit 20 may include a computer and a storage medium, where the storage medium is used for storing a program executable by the computer, and when the computer executes the program, a plurality of components of the scanner 10 are enabled to implement operations corresponding to the aforementioned imaging sequence. The data processing unit 30 is also enabled to perform predetermined data processing.

The storage media of the controller unit 20 and the data processing unit 30 may include, for example, a ROM, a floppy disk, a hard disk, an optical disk, a magneto-optical disk, a CD-ROM, or a non-volatile memory card.

The MRI system 1 further includes a worktable 40 for placing the object 16 thereon. The object 16 may be moved by a movable worktable 26 into or out of the imaging space based on the control signal from the controller unit 20.

The MRI system 1 further includes an operating console 50 connected to the controller unit 20. The operating console 50 may be disposed in an operating room or the scanning room. The controller unit 20 is used for receiving and processing an operating signal input to the operating console 50, and controlling the working state of the aforementioned components such as the worktable 40 and the scanner 10 based on the operating signal. The operating signal may include, for example, a scanning protocol or a parameter that is selected manually or automatically, where the scanning protocol may include the aforementioned imaging sequence. The controller unit 20 also controls the data processing unit 30 based on the operating signal received from the operating console 50 so as to obtain the desired image.

The operating console 50 may include a user input device, such as a keyboard and a mouse, where an operator may input an operating signal/control signal to the controller unit 20 through the user input device.

The MRI system 1 may further include a display unit 60 that may be connected to the operating console 50 to display an operation interface and may further be connected to the data processing unit 30 to display the image.

Figure 5:
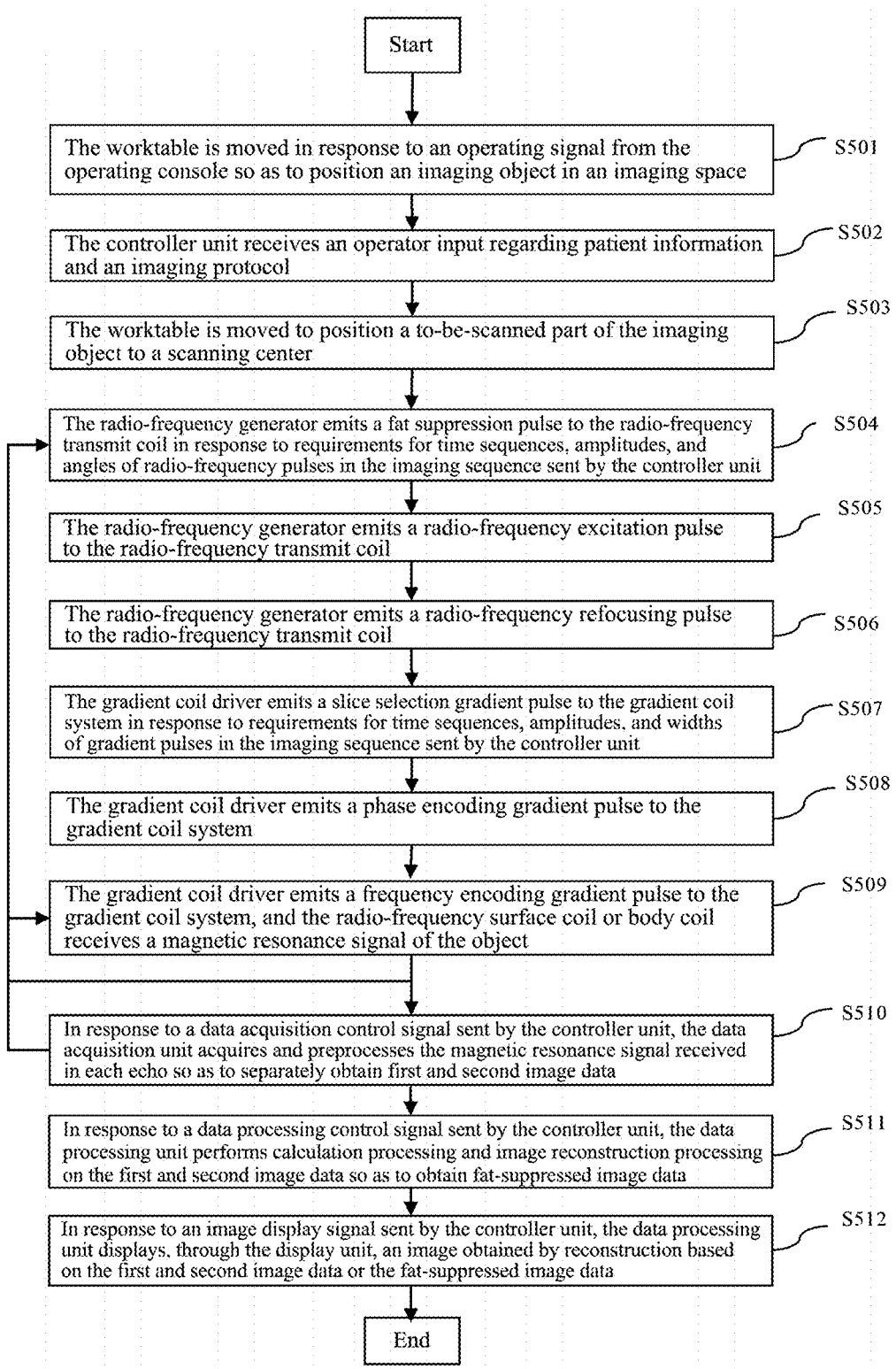
FIG. 5 is a flowchart of a method for obtaining magnetic resonance imaging data based on the MRI system 1 according to an embodiment of the present invention.

FIG. 5 is a flowchart of a method for obtaining magnetic resonance imaging data based on the MRI system 1 according to an embodiment of the present invention.

Step S501: The worktable 40 is moved in response to an operating signal from the operating console 50 so as to position an imaging object (for example, a patient) 16 in an imaging space.

Step S502: The controller unit 20 receives an operator input regarding patient information and an imaging protocol. Specifically, the operator may select the protocol based on an anatomical structure to be scanned. The imaging protocol may include a region of interest (ROI), a field of view (FOV), an imaging sequence to be performed, and the like.

Step S503: The worktable 40 is moved to position a to-be-scanned part of the imaging object 16 to a scanning center.

Step S504: The radio-frequency generator 13 emits a fat suppression pulse P41 to the radio-frequency transmit coil 12 in response to requirements for time sequences, amplitudes, and angles of radio-frequency pulses in the imaging sequence sent by the controller unit 20.

Step S505: The radio-frequency generator 13 emits a radio-frequency excitation pulse P42 to the radio-frequency transmit coil 12 in response to requirements for time sequences, amplitudes, and angles of radio-frequency pulses in the imaging sequence sent by the controller unit 20, where the radio-frequency excitation pulse P42 may be emitted immediately after the end of the fat suppression pulse P41.

Step S506: The radio-frequency generator 13 emits a radio-frequency refocusing pulse P46 to the radio-frequency transmit coil 12 in response to requirements for time sequences, amplitudes, and angles of radio-frequency pulses in the imaging sequence sent by the controller unit 20.

Step S507: The gradient coil driver 18 emits a slice selection gradient pulse to the gradient coil system 17 in response to requirements for time sequences, amplitudes, and widths of gradient pulses in the imaging sequence sent by the controller unit 20.

Step S508: The gradient coil driver 18 emits a phase encoding gradient pulse to the gradient coil system 17 in response to requirements for time sequences, amplitudes, and widths of gradient pulses in the imaging sequence sent by the controller unit 20.

Step S509: The gradient coil driver 18 emits three symmetrical frequency encoding gradient pulses (for example, gradient read pulses P43, P44, and P45) to the gradient coil system 17 in response to requirements for time sequences, amplitudes, and widths of gradient pulses in the imaging sequence sent by the controller unit 20. Magnetic resonance signals of the object are received through the radio-frequency surface coil 19 or the body coil respectively in response to the three symmetrical frequency encoding gradient pulses.

Step S510: In response to a data acquisition control signal sent by the controller unit 20, the data acquisition unit 14 acquires and preprocesses the magnetic resonance signals received in each echo so as to separately obtain first image data and second image data.

The aforementioned step S509 may be repeated many times until the current repetition time ends. After the end of the current repetition time, steps S504 to S510 are repeated to perform a next repetition time of the imaging sequence.

Step S511: In response to a data processing control signal sent by the controller unit 20, the data processing unit 30 performs calculation processing and image reconstruction processing on the first image data and the second image data so as to obtain fat-suppressed image data.

Step S512: In response to an image display signal sent by the controller unit 20, the data processing unit 30 displays, through the display unit 60, an image obtained by reconstruction based on the first image data, the second image data, or the fat-suppressed image data.

Based on the above description, an embodiment of the present invention can provide an improved magnetic resonance imaging system, including:
a scanner, the scanner used for obtaining data of an imaging object;
a controller unit, coupled to the scanner and used for controlling the scanner to perform an imaging sequence, where a fat suppression pulse is applied before the start of any repetition time of the imaging sequence; and a plurality of echoes are performed in the repetition time, where first image data when water and fat are in phase and second image data when water and fat are out of phase are obtained during each echo of the plurality of echoes; and a data processing unit, used for obtaining fat-suppressed image data according to the first image data and the second image data.

Further, the first image data and the second image data obtained during each echo have opposite chemical shift directions.

Further, during each echo, the controller unit controls the scanner to apply a first gradient read pulse when water and fat are in phase to obtain the first image data, and apply a second gradient read pulse when water and fat are out of phase to obtain the second image data, where the first gradient read pulse and the second gradient read pulse have opposite directions.

Further, the first gradient read pulse and the second gradient read pulse are continuously applied.

Further, the controller unit controls the scanner to apply a first gradient pulse once and apply a second gradient pulse twice respectively before and after the first gradient pulse during each echo.

Further, the data processing unit is used for obtaining average image data of two pieces of second image data respectively obtained when the second gradient pulse is applied twice, and obtaining the fat-suppressed image data according to the first image data and the average image data.

Figure 6:
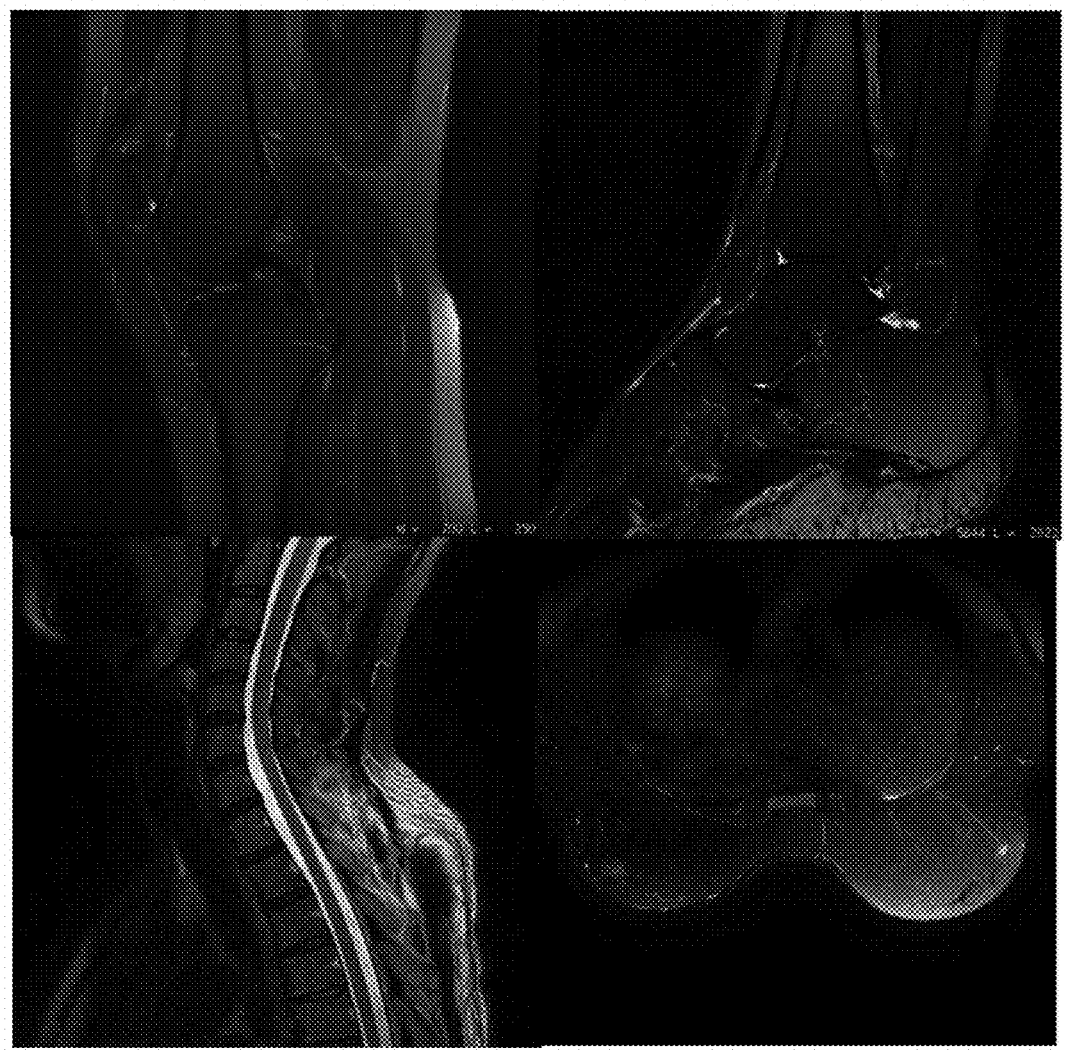
FIG. 6 illustrates a set of human tissue images obtained using an existing fat suppression technique.

FIG. 6 illustrates a set of human tissue images obtained using an existing fat suppression technique, where obvious bright signal artifact regions appear due to an undesirable fat suppression effect, resulting in an inhomogeneous image.

Figures 7, 8:
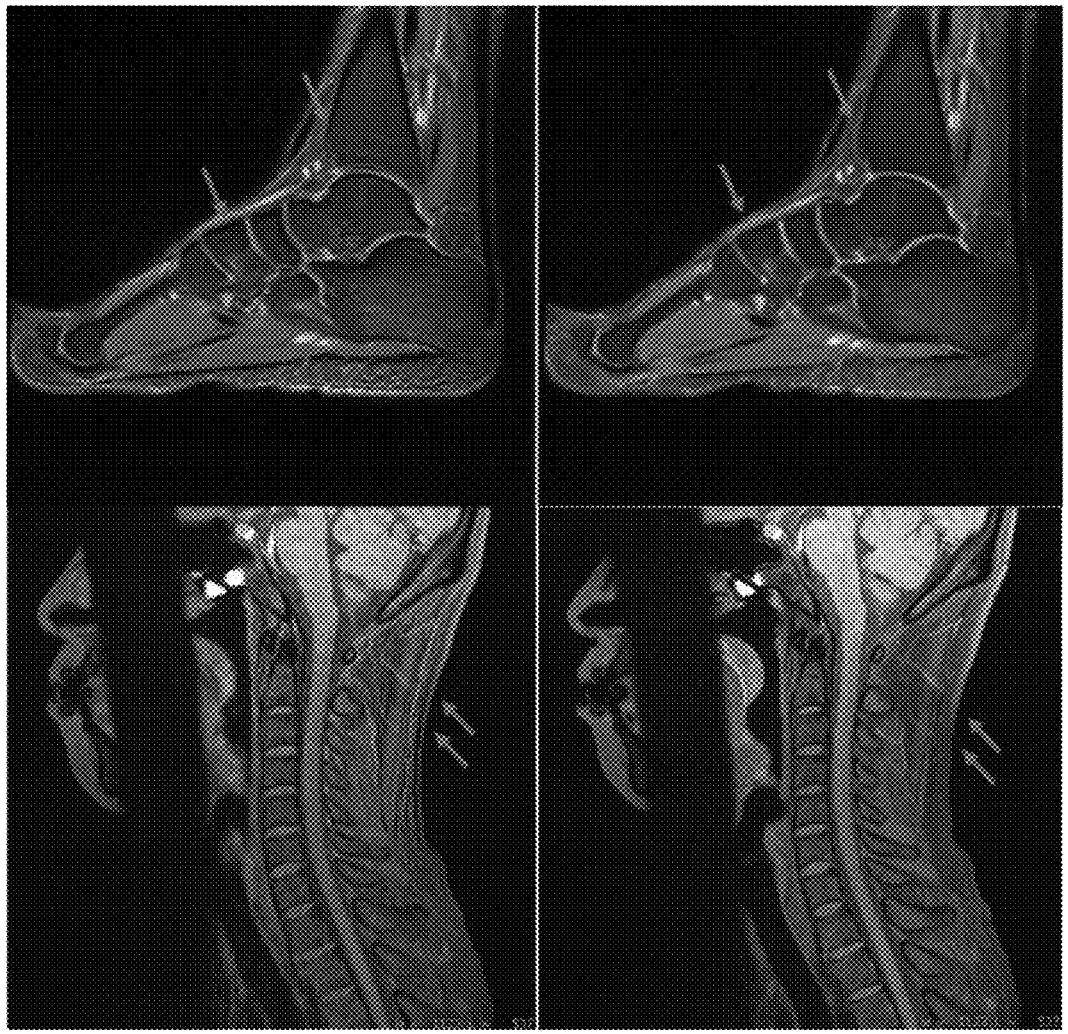
FIG. 7 and FIG. 8 each illustrates a set of human tissue images obtained using the method according to the embodiment of the present invention.

FIG. 7 and FIG. 8 each illustrates a set of human tissue images obtained using the method according to the embodiment of the present invention. FIG. 7 illustrates an image obtained when both first image data when water and fat are in phase and second image data when water and fat are out of phase are obtained during one repetition time. FIG. 8 illustrates an image obtained when a fat suppression pulse is further applied prior to the repetition time. Upon comparison between FIG. 6, FIG. 7, and FIG. 8, chemical shift artifacts and chemical shift edge artifacts are obviously eliminated in the images shown in FIG. 7 and FIG. 8. Upon comparison between the parts indicated by the arrows in FIG. 7 and FIG. 8, chemical shift edge artifacts are further eliminated in the image in FIG. 8.

As used herein, an element or step described as singular and preceded by the word "a" or "an" should be understood as not excluding such element or step being plural, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements that do not have such property. The terms "including" and "in which" are used as the plain-language equivalents of the respective terms "comprising" and "wherein." Furthermore, in the appended claims, the terms "first", "second," "third" and so on are used merely as labels, and are not intended to impose numerical requirements or a particular positional order on their objects.

This written description uses examples to disclose the present invention, including the best mode, and also to enable those of ordinary skill in the relevant art to implement the present invention, including making and using any devices or systems and performing any incorporated methods. The patentable scope of the present invention is defined by the claims, and may include other examples that occur to those skilled in the art. Such other examples are intended to be within the scope of the claims if they have structural elements that do not differ from the literal language of the claims, or if they include equivalent structural elements without substantial differences from the literal language of the claims.

The invention claimed is:

1. A method for obtaining magnetic resonance imaging data, the method comprising:
    applying a fat suppression pulse before the start of any repetition time of an imaging sequence;
    performing a plurality of echoes in the repetition time, wherein first image data when water and fat are in phase and second image data when water and fat are out of phase are obtained during each echo of the plurality of echoes;
    obtaining fat-suppressed image data according to the first image data and the second image data;
    wherein the fat suppression pulse is applied before a slice selection gradient pulse; and
    wherein a radio frequency excitation pulse is applied between the fat suppression pulse and the slice selection gradient pulse.

2. A magnetic resonance imaging system, comprising:
    a scanner, the scanner used for obtaining data of an imaging object;
    a controller unit, the controller unit coupled to the scanner and used for controlling the scanner to perform an imaging sequence, wherein a fat suppression pulse is applied before the start of any repetition time of the imaging sequence; and a plurality of echoes are performed in the repetition time, wherein first image data when water and fat are in phase and second image data when water and fat are out of phase are obtained during each echo of the plurality of echoes;
    a data processing unit, used for obtaining fat-suppressed image data according to the first image data and the second image data;
    wherein the fat suppression pulse is applied before a slice selection gradient pulse; and
    wherein a radio frequency excitation pulse is applied between the fat suppression pulse and the slice selection gradient pulse.

3. The method according to claim 1, wherein the first image data and the second image data obtained during each echo have opposite chemical shift directions.

4. The method according to claim 3, wherein during each echo, a first gradient read pulse is applied when water and fat are in phase to obtain the first image data, and a second gradient read pulse is applied when water and fat are out of phase to obtain the second image data, wherein the first gradient read pulse and the second gradient read pulse have opposite directions.

5. The method according to claim 4, wherein the first gradient read pulse and the second gradient read pulse are continuously applied.

6. The method according to claim 5, wherein a first gradient pulse is applied once and a second gradient pulse is applied twice respectively before and after the first gradient pulse during each echo.

7. The method according to claim 1, wherein the step of obtaining fat-suppressed image data according to the first image data and the second image data comprises:
obtaining the fat-suppressed image data according to the first image data and average image data of two pieces of second image data respectively obtained when the second gradient pulse is applied twice.

8. The system according to claim 2, wherein the first image data and the second image data obtained during each echo have opposite chemical shift directions.

9. The system according to claim 8, wherein during each echo, the controller unit controls the scanner to apply a first gradient read pulse when water and fat are in phase to obtain the first image data, and apply a second gradient read pulse when water and fat are out of phase to obtain the second image data, wherein the first gradient read pulse and the second gradient read pulse have opposite directions.

10. The system according to claim 9, wherein the first gradient read pulse and the second gradient read pulse are continuously applied.

11. The system according to claim 10, wherein the controller unit controls the scanner to apply a first gradient pulse once and apply a second gradient pulse twice respectively before and after the first gradient pulse during each echo.

12. The system according to claim 11, wherein the data processing unit is used for: the data processing unit is used for obtaining average image data of two pieces of second image data respectively obtained when the second gradient pulse is applied twice, and obtaining the fat-suppressed image data according to the first image data and the average image data.

13. The method according to claim 1, wherein the first image data and the second image data obtained during the same repetition time.

14. The method according to claim 1, wherein the radio-frequency excitation pulse is applied immediately after the end of the fat suppression pulse.

15. The method according to claim 14, wherein a radio-frequency refocusing pulse is applied after the end of the radio-frequency excitation pulse and before the slice selection gradient pulse.

16. The method according to claim 1, wherein the fat-suppressed image data (I3) is obtained based on an average of the first image data (I1) and the second image data (I2) and is given as I3=(I1+I2)/2.

17. The method according to claim 1, wherein the fat suppression pulse includes a heat insulation pulse.

18. The method accordingly to claim 1, wherein the first gradient read pulse and the second gradient read pulse have same amplitude and width.

* * * * *